(12) United States Patent
Kasumi

(10) Patent No.: US 12,268,514 B2
(45) Date of Patent: Apr. 8, 2025

(54) IMAGE PROCESSING APPARATUS, IMAGE PROCESSING METHOD, AND ENDOSCOPE SYSTEM

(71) Applicant: OLYMPUS MEDICAL SYSTEMS CORP., Tokyo (JP)

(72) Inventor: Makoto Kasumi, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 41 days.

(21) Appl. No.: 18/243,764

(22) Filed: Sep. 8, 2023

(65) Prior Publication Data
US 2023/0414164 A1 Dec. 28, 2023

Related U.S. Application Data

(63) Continuation of application No. PCT/JP2021/011258, filed on Mar. 18, 2021.

(51) Int. Cl.
| | |
|---|---|
| G06T 7/90 | (2017.01) |
| A61B 1/045 | (2006.01) |
| A61B 5/00 | (2006.01) |
| G06T 5/00 | (2006.01) |
| H04N 23/61 | (2023.01) |

(52) U.S. Cl.
CPC ............ A61B 5/4205 (2013.01); A61B 1/045 (2013.01); G06T 5/00 (2013.01); H04N 23/61 (2023.01); *G06T 2207/10024* (2013.01); *G06T 2207/10068* (2013.01); *G06T 2207/30004* (2013.01)

(58) Field of Classification Search
CPC ... A61B 5/4205; A61B 1/045; A61B 2560/02; A61B 1/233; A61B 5/07; A61B 1/000094; G06T 5/00; G06T 2207/10024; G06T 2207/10068; G06T 2207/30004; G06T 7/90; G06T 5/90; H04N 23/61; H04N 23/555; H04N 23/667
See application file for complete search history.

(56) References Cited

U.S. PATENT DOCUMENTS

| | | | | |
|---|---|---|---|---|
| 2009/0171190 A1* | 7/2009 | Uchiyama | ................ | A61B 5/06 318/653 |
| 2012/0162486 A1* | 6/2012 | Asakura | .................... | G06T 5/73 348/241 |

(Continued)

FOREIGN PATENT DOCUMENTS

| | | | |
|---|---|---|---|
| JP | 2009-098167 A | | 5/2009 |
| JP | 2012-217632 A | | 11/2012 |

(Continued)

OTHER PUBLICATIONS

International Search Report dated Jun. 1, 2021 received in PCT/JP2021/011258.

*Primary Examiner* — Howard D Brown, Jr.
(74) *Attorney, Agent, or Firm* — Scully, Scott, Murphy & Presser, P.C.

(57) ABSTRACT

An image processing apparatus includes a processor, in which the processor is configured to receive a picked-up image of a swallowing motion in a swallowing test in which a swallow object is provided to a subject to observe the swallowing motion, detect a color of the swallow object in the picked-up image, and perform processing for improving an image quality of the picked-up image according to a detection result of the color of the swallow object.

15 Claims, 10 Drawing Sheets

(56) References Cited

U.S. PATENT DOCUMENTS

2017/0337684 A1 11/2017 Bradley
2023/0157623 A1* 5/2023 Yanagihara .............. A61B 1/07
                                              600/476

FOREIGN PATENT DOCUMENTS

| JP | 3209885 U | 4/2017 |
| JP | 2018-015263 A | 2/2018 |
| WO | 2017/200885 A1 | 11/2017 |
| WO | 2018/225368 A1 | 12/2018 |

* cited by examiner

ORAL STAGE

PHARYNGEAL STAGE

FIG. 9

| REFERENCE COLOR | COMPLEMENTARY COLOR |
|---|---|
| YELLOW | BLUE PURPLE |
| ORANGE | BLUE |
| RED | BLUE GREEN |
| RED PURPLE | GREEN |
| PURPLE | YELLOW GREEN |

IMAGE PROCESSING APPARATUS, IMAGE PROCESSING METHOD, AND ENDOSCOPE SYSTEM

CROSS REFERENCE TO RELATED APPLICATION

This application is a continuation application of PCT/JP2021/011258 filed on Mar. 18, 2021, the entire contents of which are incorporated herein by this reference.

BACKGROUND OF THE INVENTION

1. Field of the Invention

The present invention relates to an image processing apparatus which effectively assists a swallowing test, an image processing method, and an endoscope system.

2. Description of the Related Art

Dysphagia is a disorder occurring in a series of processes of sending food from a mouth to an esophagus, and becomes a cause of aspiration pneumonia or the like in which food enters a trachea to cause inflammation. Heretofore, Japanese Patent Application Laid-Open Publication No. 2018-15263 has disclosed a technique of testing for dysphagia by using an X-ray image. However, a scale of an image diagnosis apparatus using X-rays is large. On the other hand, there is a swallowing test method of photographing, by a nasal endoscope, a series of swallowing situations after test food is put into the mouth and determining whether there is dysphagia by photographed images. A wireless endoscope may be adopted as such a nasal endoscope. Note that in the swallowing test, a test using colored test food is conducted.

Note that a general endoscope obtains observation images at a frame rate of 30 frames/second (fps) or 60 fps, for example.

SUMMARY OF THE INVENTION

An image processing apparatus according to an aspect of the present invention includes a processor, and the processor is configured to receive a picked-up image of a swallowing motion in a swallowing test in which a swallow object is provided to a subject to observe the swallowing motion, detect a color of the swallow object in the picked-up image, and perform processing for improving an image quality of the picked-up image according to a detection result of the color of the swallow object.

An image processing method according to an aspect of the present invention includes receiving a picked-up image of a swallowing motion in a swallowing test in which a swallow object is provided to a subject to observe the swallowing motion, detecting a color of the swallow object in the picked-up image, and performing processing for improving an image quality of the picked-up image according to a detection result of the color of the swallow object.

An endoscope system according to an aspect of the present invention includes an endoscope configured to obtain a picked-up image of a swallowing motion in a swallowing test in which a swallow object is provided to a subject to observe the swallowing motion, and an image processing apparatus including a communication circuit configured to receive the picked-up image, an image processing circuit configured to detect a color of the swallow object in the picked-up image, and a control circuit configured to perform processing for improving an image quality of the picked-up image according to a detection result of the image processing circuit.

BRIEF DESCRIPTION OF THE DRAWINGS

FIG. 9 is a chart illustrating an example of image quality processing in accordance with a swallow object color;

DETAILED DESCRIPTION OF THE PREFERRED EMBODIMENTS

Hereinafter, embodiments of the present invention will be described in detail with reference to the drawings.

Figure 1:
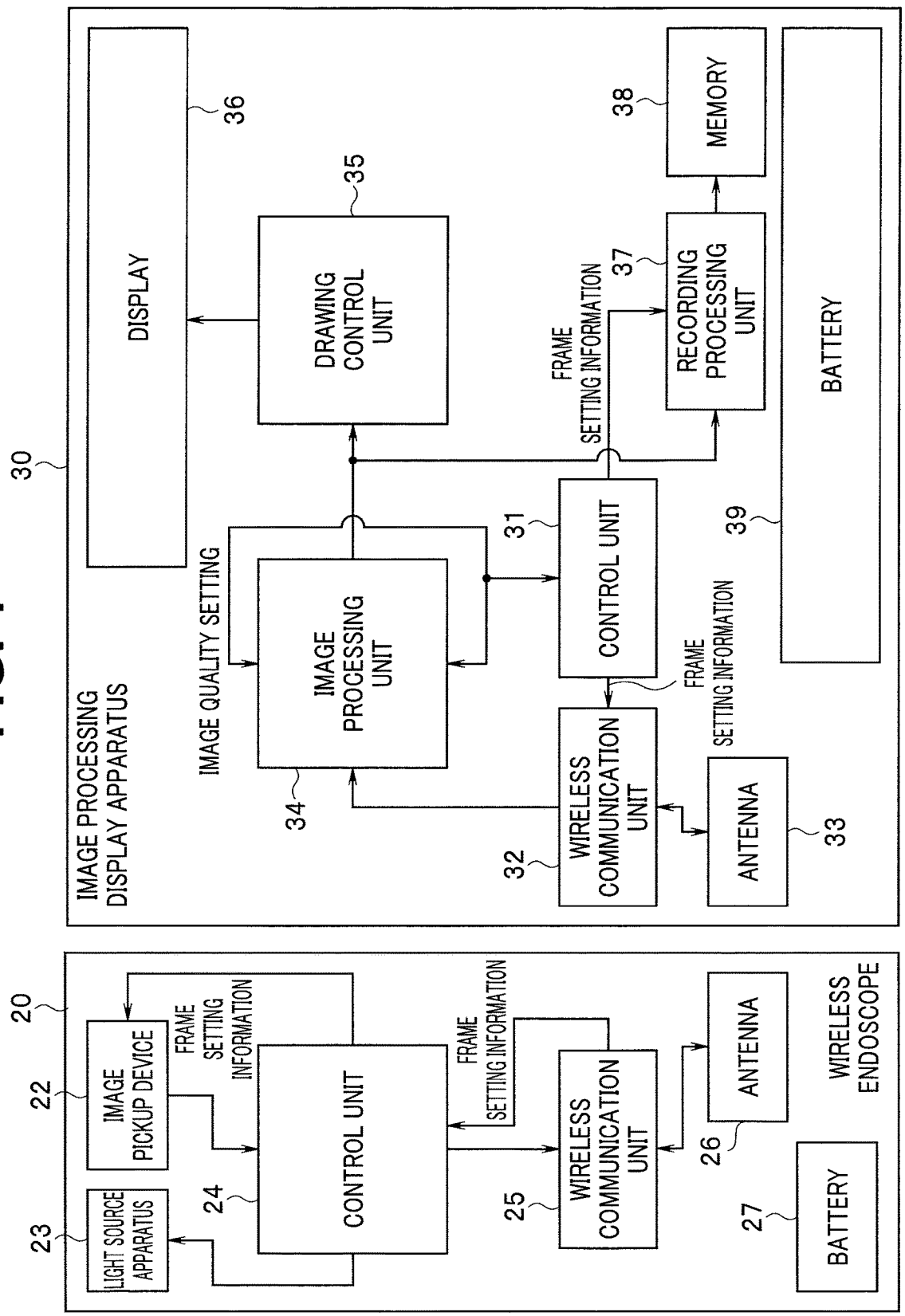
FIG. 1 is a block diagram illustrating an image processing apparatus according to an embodiment of the present invention.

FIG. 1 is a block diagram illustrating an image processing apparatus according to an embodiment of the present invention. According to the present embodiment, an image pickup frame rate during a period (hereinafter, which is referred to as an effective observation period) for obtaining an observation image considered to be particularly effective in a swallowing diagnosis at a time of a swallowing test (hereinafter, which is referred to as an effective observation image) is increased to set an image quality of the effective observation image to an image quality appropriate for an observation, and an image pickup frame rate during a period other than the effective observation period (hereinafter, which is referred to as a non-effective observation period) is decreased. Thus, according to the present embodiment, an excess increase of battery consumption in an endoscope is suppressed, and the swallowing diagnosis is effectively assisted by the effective observation image.

Figure 2:
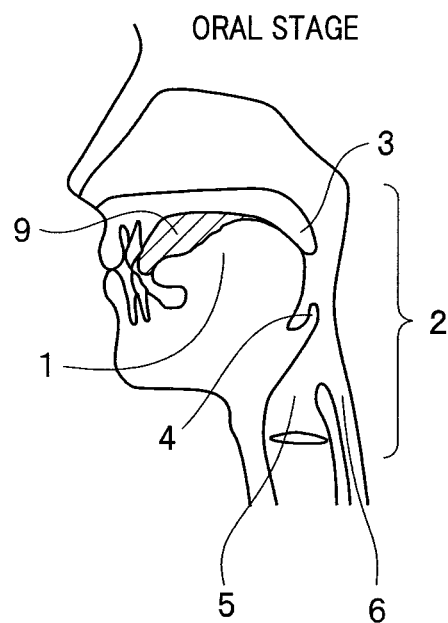
FIG. 2 is an explanatory diagram for describing a normal swallowing motion.
Figure 3:
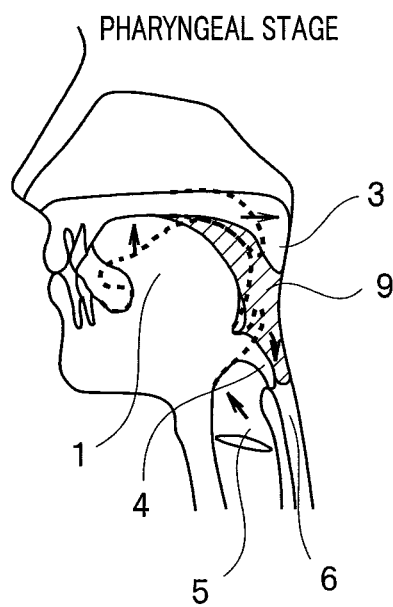
FIG. 3 is an explanatory diagram for describing the normal swallowing motion.

FIG. 2 and FIG. 3 are explanatory diagrams for describing a normal swallowing motion. FIG. 2 and FIG. 3 illustrate a mechanism of swallowing, in which FIG. 2 illustrates an oral stage, and FIG. 3 illustrates a pharyngeal stage.

FIG. 2 illustrates a state where a food bolus 9 (shaded portion) is held in an oral cavity in the oral stage. A tongue 1 rises upwards and a soft palate 3 falls downwards to partition the oral cavity and a pharynx 2. The food bolus 9 is held inside the mouth, and a state is established where the food bolus 9 may be chewed and swallowed when necessary.

Note that in the above described state, the food bolus 9 does not flow into an esophagus 6, and the epiglottis 4 rises to open an air passage 5.

When chewing is ended, due to movement of the tongue 1 and contraction of the pharynx 2, the food bolus 9 is sent from the oral cavity into the esophagus 6. FIG. 3 illustrates a state in the pharyngeal stage as described above. A broken line in FIG. 3 represents a state of the tongue 1, the soft palate 3, and the epiglottis 4 in the oral stage. Since the tongue 1, the soft palate 3, and the epiglottis 4 in the pharyngeal stage change as indicated by arrows, the food bolus 9 is sent into the esophagus 6. In the above described case, the epiglottis 4 falls (closes) to block the air passage 5, such that the food bolus 9 does not enter the air passage 5.

Note that when the food bolus 9 flows into the esophagus 6, the epiglottis 4 rises (opens) to return to an original position. The air passage 5, the oral cavity, and a nasal cavity are connected, such that breathing can be performed.

Test food or test liquid such as colored water, jelly, or yogurt having a color which is different from a color of a living body and which does not normally exist in the living body is used as the food bolus 9, so that checking of the swallowing motion is facilitated. Note that in the following description, an object which includes the test food, the test liquid, or the like and which is set as a target of the swallowing is referred to as a swallow object. In a test using the swallow object in the series of swallowing tests, a diagnosis on triggering of swallowing reflex and a diagnosis on pharyngeal clearance by swallowing of the swallow object are conducted.

In the diagnosis on the triggering of the swallowing reflex, a test is conducted with regard to (a1) that a slight laryngeal inflow of the swallow object is only observed, (a2) that a state can be observed where the swallow object reaches an epiglottic vallecula, (a3) that a state can be observed where the swallow object reaches a pyriform sinus, and (a4) that even after the swallow object reaches the pyriform sinus, the swallowing reflex does not occur fora while.

In the diagnosis on the pharyngeal clearance by the swallowing of the swallow object, a test is conducted with regard to (b1) that there is no residue of the swallow object after the swallowing, (b2) that there is a low level of residue of the swallow object, but the residue is washed out by performing dry swallowing twice or three times, (b3) that residue of the swallow object is present, and is not washed out by performing swallowing a plurality of times, and (b4) that there is a high level of residue of the swallow object, and the residue flows into a laryngeal cavity.

Figure 4:
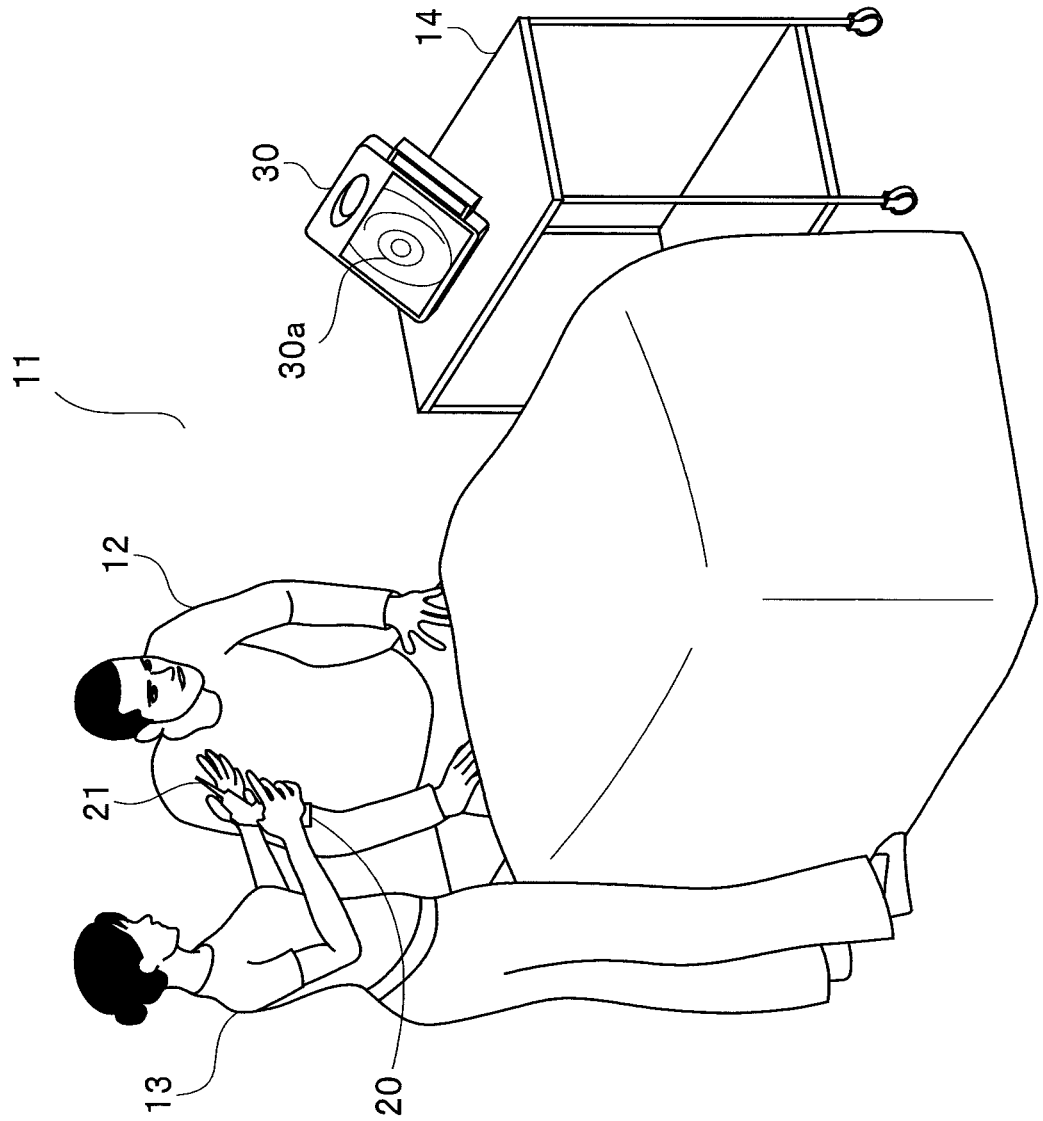
FIG. 4 is an explanatory diagram for describing a situation of a room in which a swallowing test is conducted.
Figure 5:
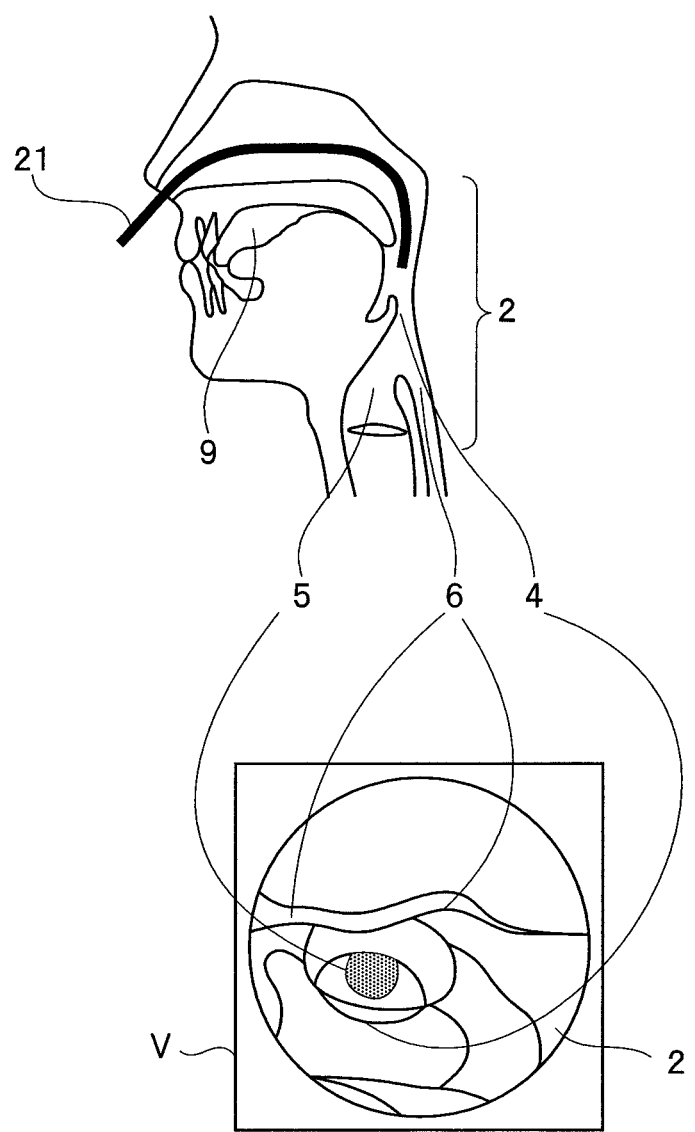
FIG. 5 is an explanatory diagram illustrating a state in which an endoscope is inserted into a nasal cavity for the swallowing test and an observation image.

FIG. 4 is an explanatory diagram for describing a situation of a room in which a swallowing test is conducted. FIG. 5 is an explanatory diagram illustrating a state in which an insertion portion 21 of an endoscope 20 is inserted into the nasal cavity for the swallowing test and an observation image V of the endoscope.

The swallowing test is conducted in a hospital room 11 or the like instead of an operation room in many cases. Consequently, a test using the wireless endoscope 20 which is easy to move as the endoscope is preferable. A subject 12 and an examiner 13 who operates the wireless endoscope 20 are present in the hospital room 11. The examiner 13 grasps the wireless endoscope 20. An image processing apparatus (hereinafter, referred to as an image processing display apparatus 30) which has a reception function and an image processing function and which includes a display apparatus is arranged on a table 14 in the hospital room 11. The wireless endoscope 20 and the image processing display apparatus 30 are configured to be able to wirelessly communicate with each other, and observation images (movie and still images) obtained by the wireless endoscope 20 are provided to the image processing display apparatus 30 to be displayed on a display screen 30a.

The endoscope 20 is provided with an image pickup device 22 (not illustrated in FIG. 5) at a distal end of the insertion portion 21 that is elongated and has flexibility. At the time of the test, as illustrated in FIG. 5, a distal end portion of the insertion portion 21 of the endoscope 20 is arranged to be stopped at an upper end of the pharynx 2, such that an optical axis of the image pickup device 22 at the distal end faces the esophagus 6. With observation images V obtained by the endoscope 20, it is possible to observe movements or the like of the pharynx 2, the esophagus 6, the swallow object (not illustrated in FIG. 5) flowing from the pharynx 2 to the esophagus 6, the air passage 5 (filled portion), and the epiglottis 4 which blocks the air passage 5.

Figure 6:
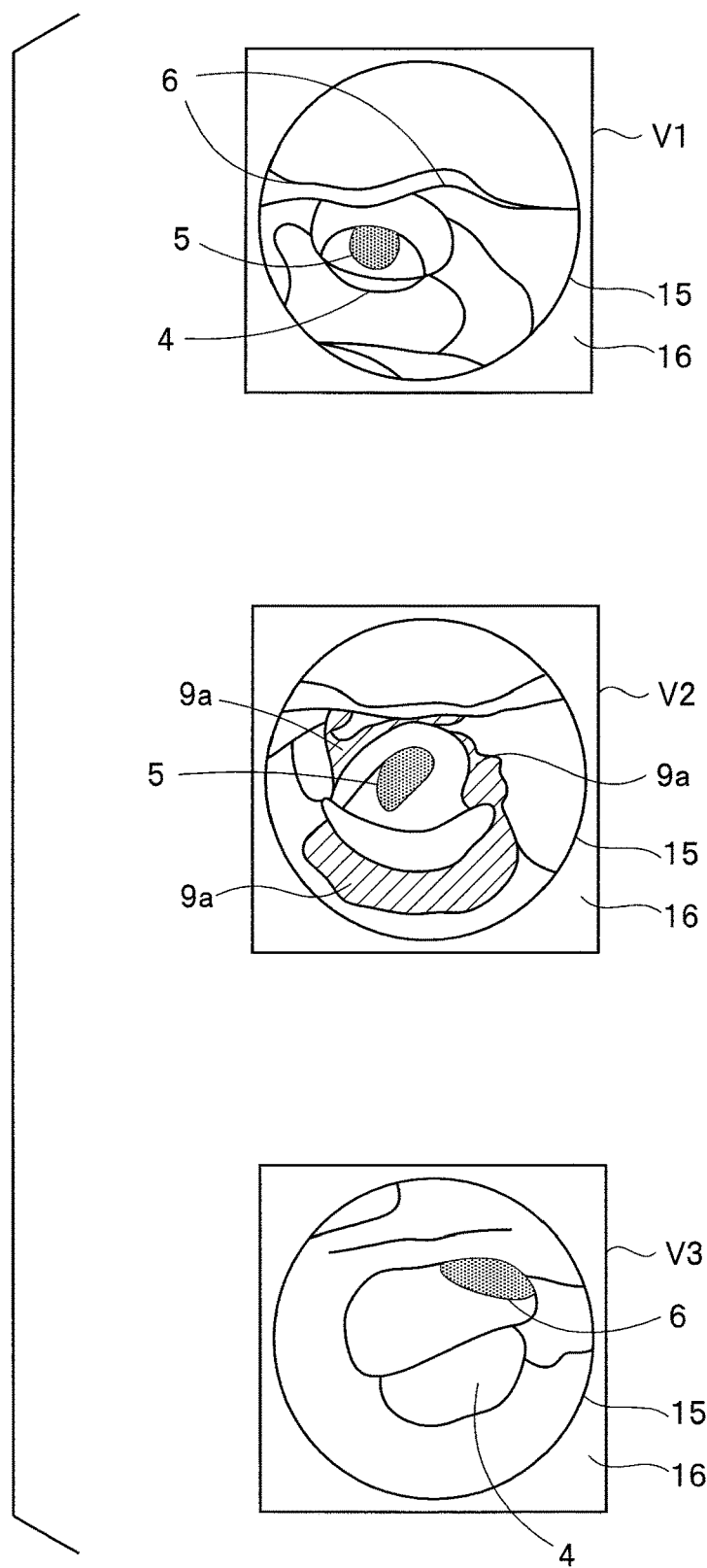
FIG. 6 is an explanatory diagram illustrating examples of observation images at a time of the swallowing test.

FIG. 6 is an explanatory diagram illustrating examples of the observation images at the time of the swallowing test. Observation images V1 to V3 in FIG. 6 each have a circular effective image region 15, and a mask region (no image region) 16 disposed in a surrounding of the effective image region 15.

The image V1 in an upper section of FIG. 6 has an image part (filled portion) of an opening of the air passage 5 at a center of the image, has an image part of the epiglottis 4 in an opened state below the image part of the air passage 5, and has image parts of the esophagus 6 in a blocked state above the image of the air passage 5 and also on the left and right of the image of the air passage 5. In other words, FIG. 5 illustrates an image in a state before the food bolus 9 flows into the pharynx 2.

The image V2 in a middle section of FIG. 6 illustrates a state in which a swallow object 9a flows into the pharynx 2 in an image part of a shaded portion. The image V3 in a bottom section of FIG. 6 illustrates a state in which the swallow object 9a flows into the esophagus 6 (filled portion), and the swallow object 9a is not observed out on the observation image, that is, a state immediately after the swallow object 9a is normally swallowed.

The images of the oral stage, the pharyngeal stage, the state immediately after the swallowing reflex, and the like are obtained by the endoscope 20, and the situation of swallowing is checked from the observation images, so that an operator can perform a diagnosis of dysphagia. In such a swallowing test, the swallow object 9a has a color of green, for example, which is different from the color of the living body. Therefore, it is facilitated to observe the situation of the inflow of the swallow object 9a from the observation images.

However, since the swallowing reflex occurs in a very short time period, it may not be easy to carry out the observation even when the swallow object 9a is colored to have a color different from the color of the living body. In view of the above, according to the present embodiment, in order that the situation of the inflow of the swallow object 9a can be reliably assessed, an image pickup frame rate of the image pickup device 22 of the wireless endoscope 20 is increased, and at a time of an observation in the image processing display apparatus 30, an image quality of the observation image to be displayed on the display screen 30a is optimized, so that an accurate diagnosis in the swallowing test is effectively assisted.

In other words, according to the present embodiment, the effective observation period is considered as a period during which observation images can be obtained which are effective for the diagnosis on the triggering of the swallowing reflex and the diagnosis on the pharyngeal clearance by the swallowing of the swallow object, and the effective observation period is determined depending on whether or not the swallow object 9a is observed in a picked-up image (observation image). According to the present embodiment, by switching the image pickup frame rate and an image quality adjustment method in the effective observation period and the non-effective observation period, the battery consumption is suppressed, convenience is ensured, and the observation images with a high medical value are provided upon the swallowing diagnosis to improve effectiveness of the diagnosis.

(Configuration)

In FIG. 1, the wireless endoscope 20 has the image pickup device 22 configuring a CCD sensor, a CMOS sensor, or the like placed in the insertion portion 21 which is not illustrated in the drawing. The wireless endoscope 20 has a light source apparatus 23. The light source apparatus 23 generates illumination light, and emits the generated illumination light towards a subject from a distal end of the insertion portion 21. The illumination light is reflected by the subject, and an optical image of the subject based on the reflected light is formed on an image pickup plane of the image pickup device 22. The image pickup device 22 performs photoelectric conversion of the optical image of the subject to obtain an image pickup output.

A control unit 24 may be configured by a processor using a central processing unit (CPU), a field programmable gate array (FPGA), or the like. The control unit 24 may control each unit through an operation according to a program stored in a memory which is not illustrated in the drawing, or may realize part or all of functions by an electronic circuit of hardware. The control unit 24 controls each unit of the wireless endoscope 20. In other words, the control unit 24 has functions as an image pickup control unit configured to control the image pickup device 22, a light source control unit configured to control the light source apparatus 23, an image processing unit configured to perform image processing, and a communication control unit configured to control a wireless communication unit 25.

The control unit 24 controls the light source apparatus 23 to adjust a quantity of the illumination light. The control unit 24 drives and controls the image pickup device 22 to control image pickup by the image pickup device 22. For example, the control unit 24 provides frame setting information to the image pickup device 22, so that the image pickup frame rate at the time of the image pickup can be adjusted. The image pickup output from the image pickup device 22 is provided to the control unit 24. The control unit 24 applies predetermined image processing such as distortion correction to the image pickup output, and then outputs the processed image pickup output to the wireless communication unit 25. Note that the image pickup output supplied from the control unit 24 to the wireless communication unit 25 is a so-called RAW image.

The wireless communication unit 25 that serves as a wireless communication circuit is controlled by the control unit 24. The wireless communication unit 25 performs modulation processing according to a predetermined wireless communication standard and converts the image pickup output into a transmission signal to be provided to an antenna 26. The antenna 26 wirelessly transmits the transmission signal from the wireless communication unit 25. The wireless transmission signal transmitted from the wireless communication unit 25 is received in the image processing display apparatus 30. The antenna 26 receives the wireless transmission signal from the image processing display apparatus 30, and provides a reception signal to the wireless communication unit 25. The wireless communication unit 25 demodulates the reception signal transmitted in the predetermined wireless communication standard to be outputted to the control unit 24.

A battery 27 is disposed inside the wireless endoscope 20. The battery 27 can supply power to each unit in the wireless endoscope 20.

The image processing display apparatus 30 has a control unit 31 configured to control each unit in the image processing display apparatus 30. The control unit 31 that serves as a control circuit may be configured by a processor using a CPU, an FPGA, or the like. The control unit 31 may operate according to a program stored in a memory which is not illustrated in the drawing to control each unit, or may realize part or all of the functions by the electronic circuit of the hardware.

An antenna 33 is disposed in the image processing display apparatus 30, and a wireless transmission signal from the wireless endoscope 20 is received by the antenna 33. A wireless communication unit 32 that serves as a wireless communication circuit is controlled by the control unit 31. The wireless communication unit 32 demodulates a reception signal received by the antenna 33 according to the predetermined wireless communication standard, and outputs a demodulation output to the control unit 31. When a transmission signal to the wireless endoscope 20 is provided from the control unit 31, the wireless communication unit 32 performs the modulation processing according to the predetermined wireless communication standard on the transmission signal, and transmits the modulated transmission signal via the antenna 33.

The control unit 31 provides, to an image processing unit 34, an image pickup output (RAW image) by the image pickup device 22 among demodulation outputs from the wireless communication unit 32. The image processing unit 34 is controlled by the control unit 31. The image processing unit 34 develops the image pickup output that is inputted and obtains a picked-up image, and applies predetermined image signal processing to the picked-up image. For example, the image processing unit 34 performs various image signal processing including various image quality setting processing such as color signal generation processing, white balance processing, y conversion processing, matrix conversion processing, and noise reduction processing. Note that the image processing unit 34 and a drawing control unit 35 which will be described below may also be configured by a processor using a CPU, an FPGA, or the like. The image processing unit 34 and the drawing control unit 35 may operate according to a program stored in a memory which is not illustrated in the drawing to control each unit, or may realize part or all of the functions by the electronic circuit of the hardware.

According to the present embodiment, the image processing unit 34 determines, by image processing, whether or not the swallow object exists in a photographing range of the image pickup device 22, that is, whether or not the image part of the swallow object exists in the picked-up image obtained by the image pickup by the image pickup device 22. For example, the image processing unit 34 may determine a color of each pixel in the picked-up image. When pixels with a same color as a color of the swallow object exist as a block in a predetermined region, the image processing unit 34 may regard the predetermined region as an image region corresponding to the swallow object (hereinafter, referred to as a swallow object image region) and obtain a judgement result indicating that the image part of the swallow object exists in the picked-up image. The image processing unit 34 outputs to the control unit 31 the judgement result on whether or not the image part of the swallow object exists in the picked-up image. For example, the image processing unit 34 may output the judgement result for each frame.

In other words, a judgement result indicating that the image part of the swallow object exists in the picked-up image (hereinafter, referred to as an inflow detection judgement result) or a judgement result indicating that the image part of the swallow object does not exist in the picked-up image (hereinafter, referred to as a non-inflow detection judgement result) is provided to the control unit 31 from the image processing unit 34. In other words, according to the present embodiment, a period during which the inflow detection judgement result is obtained is the effective observation period, and a period during which the non-inflow detection judgement result is obtained is the non-effective observation period.

In an initial setting immediately after start of the swallowing test, the control unit 31 generates frame setting information in which an image pickup frame rate for the image pickup by the image pickup device 22 is set as a reference frame rate. When the inflow detection judgement result is provided from the image processing unit 34, the control unit 31 generates frame setting information to set the image pickup frame rate for the image pickup by the image pickup device 22 to a frame rate higher than the reference frame rate (hereinafter, referred to as a high frame rate), and outputs the frame setting information to the wireless communication unit 32.

When the output of the image processing unit 34 is changed from the inflow detection judgement result to the non-inflow detection judgement result, in a case where the non-inflow detection judgement result continues for a predetermined time period (for example, for several seconds) without interruption, the control unit 31 may generate frame setting information for returning the image pickup frame rate for the image pickup by the image pickup device 22 to the reference frame rate, and output the frame setting information to the wireless communication unit 32.

The frame setting information generated by the control unit 31 is transmitted from the antenna 33 by the wireless communication unit 32. When the frame setting information transmitted from the antenna 33 is received, the antenna 26 of the wireless endoscope 20 outputs the frame setting information to the control unit 24. When the frame setting information from the image processing display apparatus 30 is received, the control unit 24 adjusts the image pickup frame rate of the image pickup device 22 according to the frame setting information. Note that power consumption at the time of image pickup at the high frame rate in the wireless endoscope 20 is larger than power consumption at the time of image pickup at a standard frame rate.

After the inflow detection judgement result is outputted, the image pickup output obtained by the image pickup at a frame rate higher than the reference frame rate (hereinafter, referred to as a high frame rate) is provided to the image processing unit 34 of the image processing display apparatus 30. When the inflow detection judgement result is obtained, the image processing unit 34 determines a color of the swallow object image region as a swallow object color. The image processing unit 34 performs image setting to emphasize a component of a complementary color of the swallow object color for a region other than the swallow object image region in the picked-up image, and applies to the picked-up image the image processing according to the image setting.

Note that the image processing unit 34 continues the emphasis processing until the non-inflow detection judgement result is obtained. The image processing unit 34 outputs the picked-up image after the image processing to the drawing control unit 35 and a recording processing unit 37.

The drawing control unit 35 that serves as a drawing control circuit applies drawing processing for drawing the input picked-up image to the picked-up image, and then outputs the processed picked-up image to a display 36. The display 36 displays the picked-up image from the drawing control unit 35 on the display screen 30a. In other words, the display 36 performs display at the standard frame rate for the picked-up images obtained by the image pickup at the standard frame rate by the wireless endoscope 20, and performs display at the high frame rate for the picked-up images obtained by the image pickup at the high frame rate by the wireless endoscope 20.

The frame setting information is also provided to the recording processing unit 37 configuring a recording apparatus from the control unit 31. The recording processing unit 37 performs recording processing of the picked-up images from the image processing unit 34 at a frame rate designated by the frame setting information to record the picked-up images in a memory 38. Note that the memory 38 may be a predetermined recording medium which can record information and may also be configured, for example, by a memory medium such as a flash memory or a magnetic medium such as a hard disc. The recording processing unit 37 can perform recording in a format corresponding to a format of the memory 38.

A battery 39 is disposed inside the image processing display apparatus 30. The battery 39 can supply power to each unit in the image processing display apparatus 30. Note that the image processing display apparatus 30 is used in a state of being installed on a table or the like, but the wireless endoscope 20 is used by being grasped by the examiner 13, so that the battery 27 has a smaller capacity than a capacity of the battery 39.

(Action)

Figure 7:
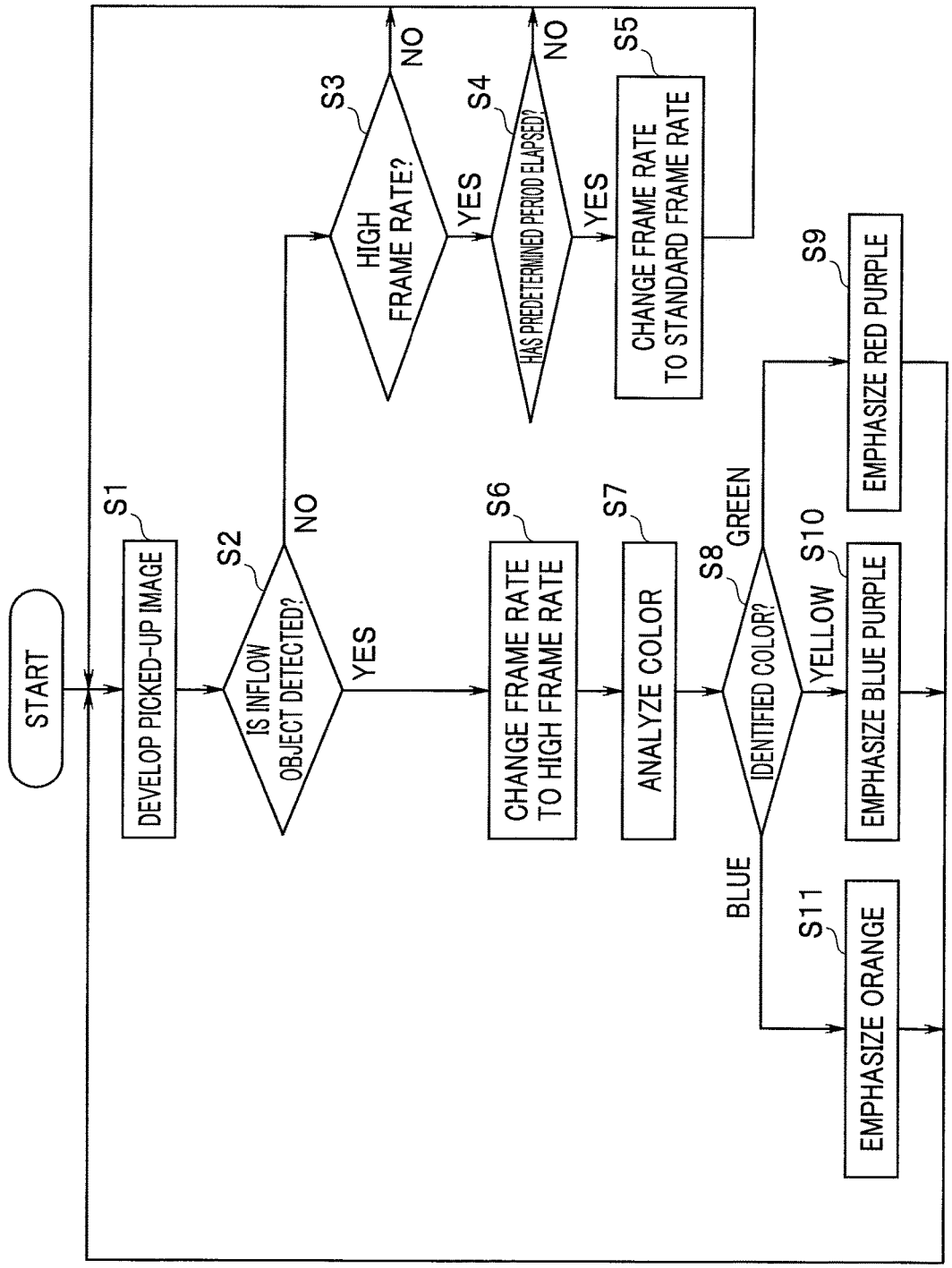
FIG. 7 is a flowchart for describing an operation of the embodiment.
Figure 8:
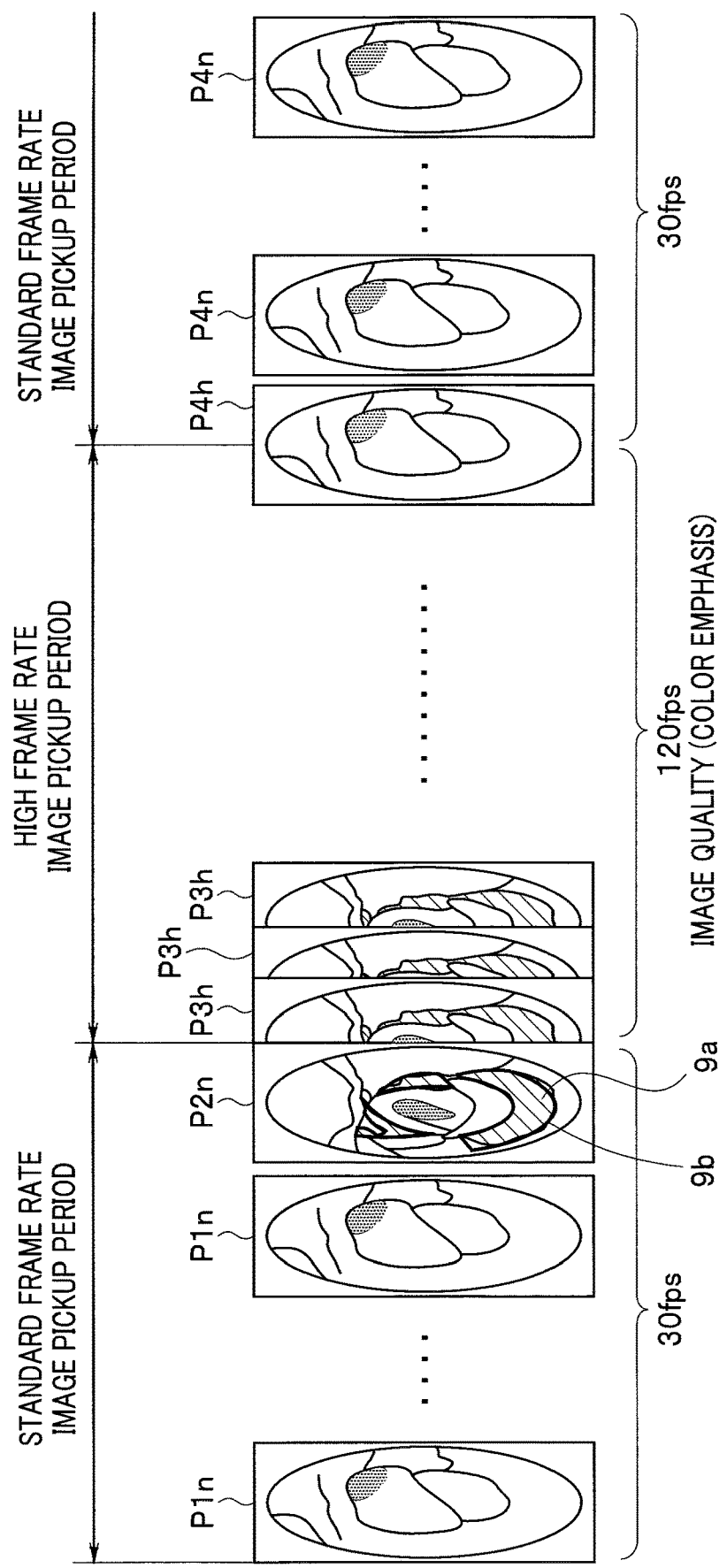
FIG. 8 is an explanatory diagram for describing the operation of the embodiment.
Figure 10:
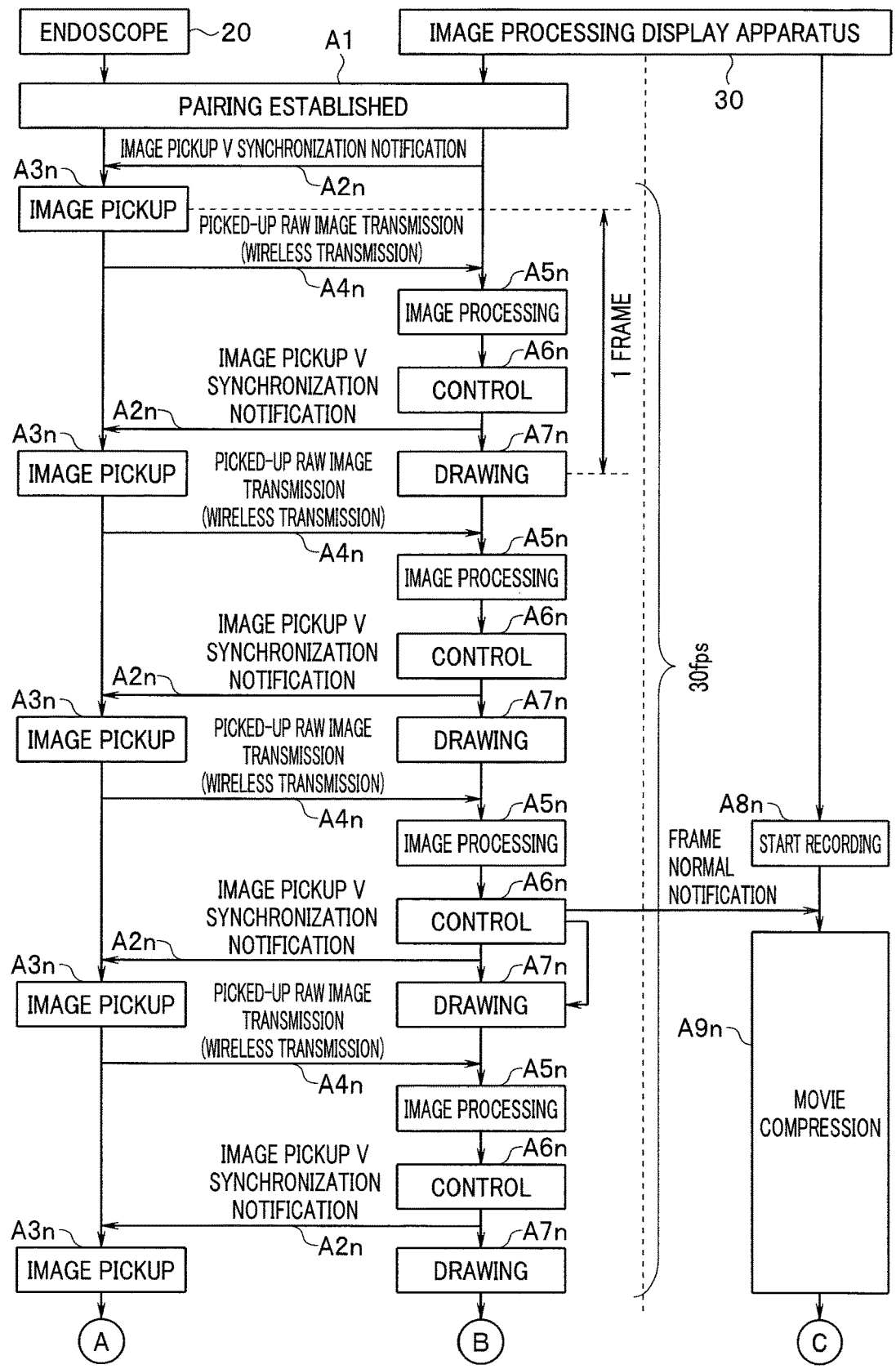
FIG. 10 is a sequence diagram illustrating a processing sequence in a wireless endoscope 20 and an image processing display apparatus 30.
Figure 11:
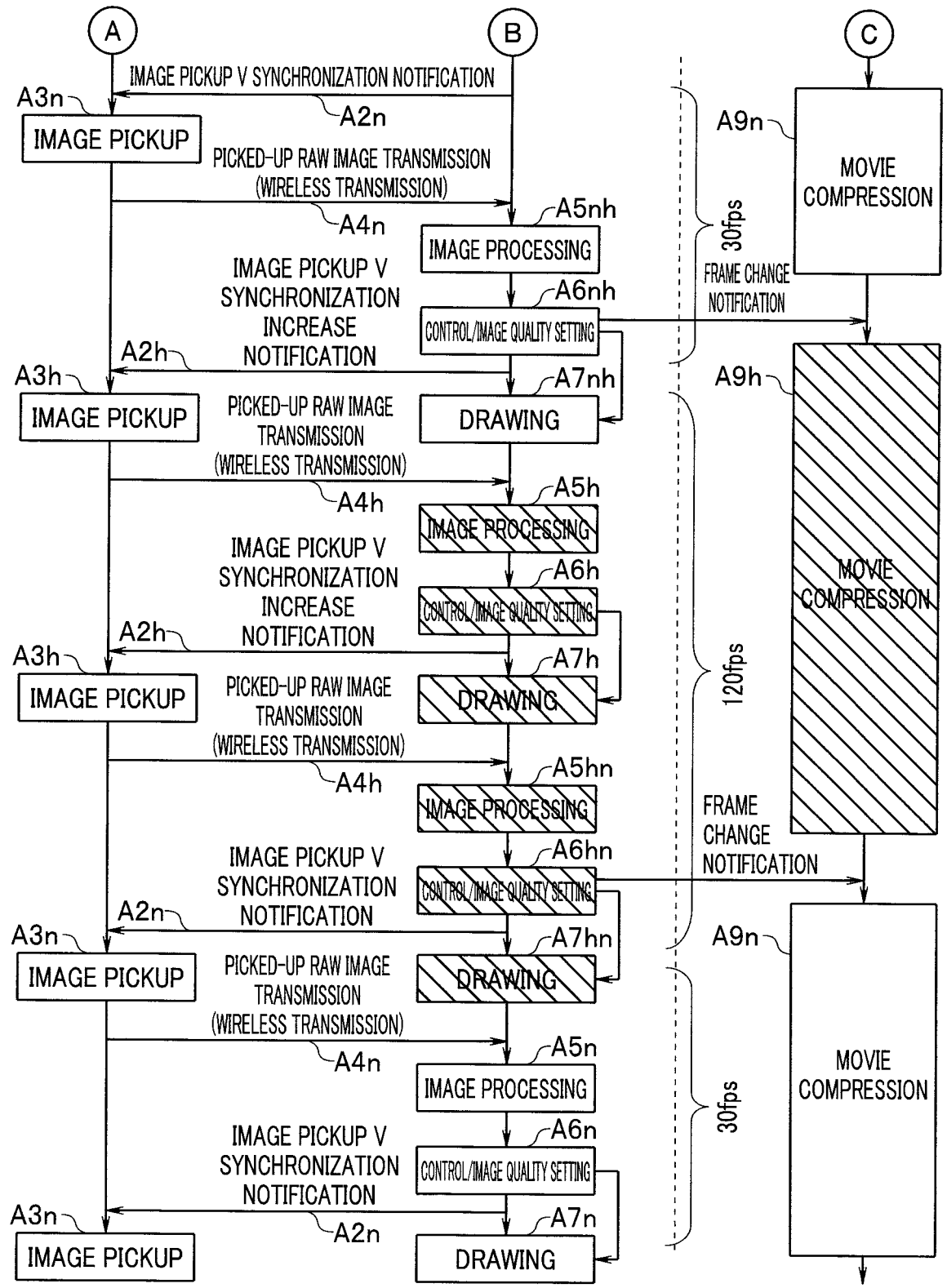
FIG. 11 is a sequence diagram illustrating the processing sequence in the wireless endoscope 20 and the image processing display apparatus 30.

Next, an operation of an embodiment configured as described above will be described with reference to FIG. 7 to FIG. 11. FIG. 7 is a flowchart for describing the operation of the embodiment, and FIG. 8 is an explanatory diagram for describing the operation of the embodiment. FIG. 7 illustrates processing of each unit of the image processing display apparatus 30. A horizontal axis in FIG. 8 represents time, and a series of picked-up images obtained in a swallowing test are arranged along a time axis. Note that by taking into account a size of a sheet in FIG. 8, each of the picked-up images is illustrated in a state of being compressed in a horizontal direction. FIG. 9 is a chart illustrating an example of image quality processing in accordance with a swallow object color. FIG. 10 and FIG. 11 are sequence diagrams illustrating a processing sequence in the wireless endoscope 20 and the image processing display apparatus 30. Note that in FIG. 10 and FIG. 11, encircled letters indicate that processing is connected between identical letters. Note that in FIG. 10 and FIG. 11, a suffix n indicates processing at a standard frame rate, a suffix h indicates processing at a high frame rate, a suffix nh indicates processing at a time of transition from the standard frame rate to the high frame rate, and a suffix hn indicates processing at a time of transition from the high frame rate to the standard frame rate.

Upon the swallowing test, initial setting is performed in the wireless endoscope 20 and the image processing display apparatus 30. As illustrated in FIG. 10, pairing is implemented between the wireless communication unit 25 of the wireless endoscope 20 and the wireless communication unit 32 of the image processing display apparatus 30. When the pairing is established (A1), the control unit 31 of the image processing display apparatus 30 causes the wireless communication unit 32 to transmit frame setting information for deciding an image pickup frame rate of the image pickup device 22 (A2n). For example, the frame setting information may be a notification for deciding vertical synchronization timing at the time of image pickup of the image pickup device 22 (image pickup V synchronization notification), and the notification is transmitted for each frame, for example. The control unit 24 of the wireless endoscope 20 drives the image pickup device 22 according to the notification, and sets the image pickup frame rate of the image pickup device 22 to the standard frame rate such as 30 fps or 60 fps.

The image pickup device 22 performs image pickup at the standard frame rate (A3n), and outputs the image pickup output obtained by the image pickup to the control unit 24. Note that in FIG. 10 and FIG. 11, the image pickup (A3n) is discretely illustrated, but is continuously performed at the designated image pickup frame rate. In FIG. 10 and FIG. 11, due to a space of the sheet, only a small number of frames are illustrated for the image pickup, but in actuality, the image pickup is performed for a time period of the swallowing test.

In the swallowing test, the wireless endoscope 20 is inserted into the nasal cavity, and the distal end portion of the insertion portion 21 of the wireless endoscope 20 is caused to stop at a position (test position) at the upper end of the pharynx 2 where the pharynx 2 can be observed. The swallowing test is started in the above described state. In other words, first, the examiner 13 instructs a subject to put a swallow object such as test food and test water into the mouth and hold the swallow object in the oral cavity. In the above described state, images P1n in FIG. 8 are obtained. The plurality of images P1n in FIG. 8 are images before the swallow object flows into the pharynx 2 immediately after the test start, and are obtained by the image pickup at the standard frame rate. Note that before the swallowing test using the swallow object, dry swallowing without using the swallow object may also be implemented.

After image processing is applied to the image pickup output of the image pickup device 22, the control unit 24 causes the wireless communication unit 25 to transmit the image pickup output to the image processing display apparatus 30 via the antenna 26 (A4n). The wireless communication unit 32 of the image processing display apparatus 30 supplies the image pickup output received via the antenna 33 to the image processing unit 34. The image processing unit 34 performs image processing on the image pickup output (A5n). In other words, in step S1 of FIG. 7, the image processing unit 34 develops and applies predetermined image processing to the image pickup output to be then outputted to the drawing control unit 35. The drawing control unit 35 executes drawing processing for causing the picked-up image to be displayed on the display 36 (A7n). Accordingly, the picked-up image obtained by the image pickup device 22 of the wireless endoscope 20 is displayed by the drawing control unit 35 on the display screen 30a of the display 36.

Note that in the image processing (A5n), image processing for obtaining the inflow detection judgement result or the non-inflow detection judgement result is also performed. In step S2 of FIG. 7, the image processing unit 34 of the image processing display apparatus 30 determines by the image processing whether or not the image part of the swallow object exists in the picked-up image. The image processing unit 34 outputs to the control unit 31 the inflow detection judgement result or the non-inflow detection judgement result which is the judgement result in the above described case.

According to the present embodiment, after the image processing (A5n), the control unit 31 implements control (A6n) on the image pickup frame rate based on the inflow detection judgement result or the non-inflow detection judgement result. When the inflow detection judgement result is inputted, the control unit 31 shifts the processing from step S2 to step S3 to determine whether or not the image pickup at the high frame rate is performed. During a period (standard frame rate image pickup period in FIG. 8) up to a time point before an image of the swallow object is picked up, the image pickup at the standard frame rate is performed, and the image processing unit 34 returns the processing from step S3 to step S1.

From the start of the swallowing test until an image of the swallow object 9a is picked up, the non-inflow detection judgement result is outputted from the image processing unit 34, and A2n to A7n in FIG. 10 are repeated at the standard frame rate. Note that in the control (A6n), the control unit 31 also provides information on a frame rate of the picked-up image (frame normal notification indicating the standard frame rate) to the drawing control unit 35.

Furthermore, for example, when a recording instruction is generated by the examiner 13 or the like, in the control (A6n) in FIG. 10, the control unit 31 provides the picked-up images from the image processing unit 34 to the recording processing unit 37 too to cause the recording processing unit 37 to start recording of the picked-up images (A8n). The recording processing unit 37 hereinafter performs movie compression recording of the picked-up images in the memory 38 (A9n). Note that in the control (A6n), the control unit 31 also provides information on the frame rate of the picked-up images (frame normal notification indicating the standard frame rate) to the recording processing unit 37.

Here, it is assumed that the examiner 13 issues a swallowing instruction. The subject 12 swallows the swallow object according to the swallowing instruction by the examiner 13. In other words, the tongue of the subject 12 rises, and the throat moves in conjunction with the above described movement, such that the swallow object 9a is sent into the pharynx 2. The image pickup device 22 picks up an image of the pharynx 2, and the image part of the swallow object 9a is included in the picked-up image.

An image P2n in FIG. 8 represents a picked-up image in the above described case, and the image part of the swallow object 9a is illustrated by the shaded portion. The image is displayed on the display screen 30a of the display 36 by the drawing control unit 35 (A7nh). In step S2 in FIG. 7, when it is determined by the image processing that the image part of the swallow object 9a exists in the picked-up image, the image processing unit 34 of the image processing display apparatus 30 outputs the inflow detection judgement result to the control unit 31. For example, it is assumed that the swallow object 9a is colored green. In the above described case, when a color of each pixel in the picked-up image is determined and pixels with a same color of green exist as a block in a predetermined region, the predetermined region is assumed to be a swallow object image region 9b corresponding to the swallow object 9a which is colored green, and the image processing unit 34 outputs the inflow detection judgement result indicating that the swallow object image region 9b that is the image part of the swallow object 9a exists in the picked-up image (A5*nh* in FIG. 11). When the inflow detection judgement result is provided, the control unit 31 shifts the processing from step S2 to step S6.

In step S6 (A6*nh* in FIG. 11), the control unit 31 generates frame setting information for changing the image pickup frame rate by the image pickup device 22 from the standard frame rate to the high frame rate. The frame setting information is transmitted by the wireless communication unit 32 to the wireless endoscope 20 via the antenna 33 (A2*h*). Note that the frame setting information in the above described case may also be, for example, a notification for shortening a vertical synchronization period (image pickup V synchronization increase notification) at the time of the image pickup of the image pickup device 22.

When the frame setting information is received, the wireless communication unit 25 of the wireless endoscope 20 provides the frame setting information to the control unit 24. Thus, the control unit 24 performs control to change the image pickup frame rate of the image pickup device 22 according to the frame setting information. Accordingly, the image pickup device 22 performs the image pickup at the high frame rate (A3*h*). As described above, when the swallow object 9*a* is detected in the pharynx 2, the image pickup frame rate of the image pickup device 22 is changed to the high frame rate, and hereinafter the image pickup is performed at the high frame rate of 120 fps, for example. Note that in FIG. 10, the image pickup (A3*h*) is discretely illustrated, but the image pickup is continuously performed at the designated high frame rate.

The high frame rate image pickup period in FIG. 8 indicates a period during which the high frame rate image pickup is performed. The image pickup output picked up and obtained at the high frame rate is provided to the image processing display apparatus 30 (A4*h*). During the high frame rate image pickup period, the image processing unit 34 of the image processing display apparatus 30 performs the image processing on the image pickup output that is picked up and obtained at the high frame rate (A5*h*). Note that during the above described period, the power consumption of the wireless endoscope 20 increases.

In A6*h* in FIG. 11, when the inflow detection judgement result is provided from the image processing unit 34, the control unit 31 instructs image quality setting for the image processing unit 34 in accordance with a color of the swallow object 9*a*. In A6*h*, the image processing unit 34 analyzes the color of the swallow object. In step S7, the image processing unit 34 determines a swallow object image region 6*b* as the swallow object color. The image processing unit 34 sets an image quality with which the swallow object image region 6*b* is conspicuously identifiable in the picked-up image according to the judgement result of the swallow object color such that a change in an image part of a swallow object 6*a* is clarified. For example, the image processing unit 34 performs an image setting to emphasize a component of a complementary color of the swallow object color for a region other than the swallow object image region 9*b* in the picked-up image, and applies the image processing according to the image setting to the picked-up image. Note that when the image quality setting to emphasize the component of the complementary color is performed, a color which is a color other than the color of the living body and which is not an achromatic color is adopted as the color of the swallow object 9*a*.

Accordingly, picked-up images P3*h* of FIG. 8 in which the component of the complementary color of the swallow object color is emphasized for the region other than the swallow object image region 9*b* are obtained. As illustrated in FIG. 9, for example, when the swallow object is green, a complementary color is red purple. In the above described case, in step S9, the image processing unit 34 performs image processing to emphasize a component of red purple which is the complementary color for the region other than the swallow object image region 9*b*. When the swallow object is yellow, for example, a complementary color is blue purple. In the above described case, in step S10, the image processing unit 34 performs image processing to emphasize a component of blue purple for the region other than the swallow object image region 9*b*. When the swallow object is blue, for example, a complementary color is orange. In the above described case, in step S11, the image processing unit 34 performs image processing to emphasize a component of orange for the region other than the swallow object image region 9*b*.

The image processing unit 34 outputs the picked-up image after the image processing to the drawing control unit 35 and the recording processing unit 37. During the high frame rate image pickup period, the adjustment is made to such an image quality that it is easy to clearly distinguish the color of the swallow object 9*a* and the color of the region other than the swallow object image region 9*b* from each other, and the smooth picked-up images are displayed on the display screen 30*a* of the display 36 due to the high frame rate (A7*h*), and movie compression recording is performed as a movie file by the recording processing unit 37 (A9*h*). Since the picked-up images of the swallowing motion are recorded at the high frame rate, it is possible to check the high speed swallowing motion in detail even when the recorded picked-up images are reproduced frame by frame.

When swallowing is normally performed, by the swallowing reflex of the subject 12, the epiglottis 4 blocks the air passage 5, and the pharynx 2 contracts to send the swallow object 9*a* into the esophagus 6. The epiglottis 4 returns to the original position, and air flows through the air passage 5. Then, the swallow object 9*a* is out of an image pickup range, and the image part of the swallow object 9*a* is no longer included in the picked-up image. A picked-up image P4*h* in FIG. 8 represents an image obtained in the above described case.

Thus, the image processing unit 34 determines that the image part of the swallow object 9*a* is no longer included in the picked-up image, and outputs the non-inflow detection judgement result to the control unit 31 (A5*hn* in FIG. 11). In step S3, when it is determined that a current period is the high frame rate image pickup period, the control unit 31 determines whether or not a predetermined period (for example, several seconds) elapses in the following step S4. Until the predetermined period elapses, S1 to S4 are repeated. When the predetermined period has elapsed after the image part of the swallow object is no longer included in the picked-up image, the control unit 31 determines that the swallow object 9*a* does not remain in the pharynx 2 or trachea, and generates frame setting information to return the image pickup frame rate to the standard frame rate (A6*hn*). The frame setting information is supplied to the control unit 24 via the wireless communication unit 32, the antenna 33, the antenna 26, and the wireless communication unit 25 (A2*n*). The control unit 24 returns the image pickup frame rate of the image pickup device 22 to the standard frame rate (A3*n*). Thus, hereinafter, the power consumption of the wireless endoscope 20 is reduced. Accordingly, the image pickup at the standard frame rate is hereinafter performed, and picked-up images P4*n* in FIG. 8 are obtained.

As described above, in the swallowing test, the wireless endoscope 20 picks up the image of the state before the swallow object is to be swallowed, the image of the state at a moment when the swallow object is swallowed, and the image of the state after the swallow object is swallowed. In the above described case, during the high frame rate image pickup period when and after the swallow object reaches the pharynx 2, the picked-up images are obtained at the high frame rate. As a result, the checking of the flow of the swallow object or the like is facilitated also with regard to the swallowing reflex which is performed during a relatively short time period. During the high frame rate image pickup period, the image quality setting at which the distinguishment between the swallow object and the living body is facilitated is applied to the picked-up image, so that the checking of the swallow object or the like is further facilitated. The high frame rate image pickup period during which the power consumption increases is set to have a relatively short time period from a time point when the swallow object is included in the image pickup range of the image pickup device 22 until the swallowing reflex ends and the swallow object is no longer included in the image pickup range. According to the present embodiment, the increase of the power consumption is suppressed, and the picked-up image effective for the swallowing diagnosis is obtained.

Note that even after the swallow object moves to the esophagus 6 after the swallowing reflex ends, dysphagia in which the swallow object remains in the pharynx 2 may be confirmed. In view of the above, in step S2, after the swallow object is detected, in a case where the swallow object is still detected even after a predetermined time period has elapsed, it is assumed that dysphagia in which the swallow object remains is occurring. The control unit 31 may generate frame setting information for forcedly stopping the image pickup at the high frame rate to return to the image pickup at the standard frame rate.

As described above, according to the present embodiment, by detecting the swallow object, the high frame rate image pickup period is set, and the image quality setting is applied to facilitate identification of the swallow object. The increase of the power consumption is suppressed, and the convenience is ensured. The observation image with a high medical value is provided upon the swallowing diagnosis to be able to improve the effectiveness of the diagnosis.

Note that in the above explanation, the wireless endoscope is described as a swallowing endoscope as an example, but the configuration may also be applied to an endoscope configured to transmit an image pickup output by using a cable.

The present invention is not directly limited to the respective embodiments described above, but can be embodied in an implementation stage by alternating the components in a scope without departing from a gist of the present invention. Various inventions can be formed by appropriate combinations of the plurality of components disclosed in the respective embodiments described above. For example, some components of all components illustrated in the embodiments may also be deleted. Furthermore, components across different embodiments may also be appropriately combined.

What is claimed is:

1. An image processing apparatus comprising:
a processor, wherein the processor is configured to
receive a picked-up image of a swallowing motion in a swallowing test in which a swallow object is provided to a subject to observe the swallowing motion,
detect a color of the swallow object in the picked-up image, and
perform processing for improving an image quality of the picked-up image according to a detection result of the color of the swallow object.

2. The image processing apparatus according to claim 1, wherein
the processor performs control to change an image pickup frame rate at a time of image pickup of the swallowing motion.

3. The image processing apparatus according to claim 1, wherein
the processor instructs image processing for facilitating identification of the swallow object in the picked-up image.

4. The image processing apparatus according to claim 2, wherein
the processor sets the image pickup frame rate at the time of the image pickup of the swallowing motion to be higher than a standard frame rate when the swallow object is detected in the picked-up image, and sets the image pickup frame rate at the time of the image pickup of the swallowing motion to the standard frame rate when the swallow object is not detected in the picked-up image.

5. The image processing apparatus according to claim 3, wherein
the processor performs image quality setting to emphasize a complementary color component of the color of the swallow object for a region other than an image region of the swallow object in the picked-up image.

6. The image processing apparatus according to claim 2, wherein
the processor performs drawing control for causing a display apparatus to display the picked-up image, the image pickup frame rate of which is different.

7. The image processing apparatus according to claim 2, wherein
the processor performs recording processing for recording the picked-up image, the image pickup frame rate of which is different.

8. An image processing method comprising:
receiving a picked-up image of a swallowing motion in a swallowing test in which a swallow object is provided to a subject to observe the swallowing motion:
detecting a color of the swallow object in the picked-up image; and
performing processing for improving an image quality of the picked-up image according to a detection result of the color of the swallow object.

9. The image processing method according to claim 8, wherein
an image pickup frame rate at a time of image pickup of the swallowing motion is set to be higher than a standard frame rate when the swallow object in the picked-up image is detected, and the image pickup frame rate at the time of the image pickup of the swallowing motion is set to the standard frame rate when the swallow object is not detected in the picked-up image.

10. The image processing method according to claim 8, wherein
image quality setting is performed to emphasize a complementary color component of the color of the swallow object for a region other than an image region of the swallow object in the picked-up image.

11. An endoscope system comprising:
an endoscope configured to obtain a picked-up image of a swallowing motion in a swallowing test in which a swallow object is provided to a subject to observe the swallowing motion; and
an image processing apparatus including a communication circuit configured to receive the picked-up image, an image processing circuit configured to detect a color of the swallow object in the picked-up image, and a control circuit configured to perform processing for improving an image quality of the picked-up image according to a detection result of the image processing circuit.

12. The endoscope system according to claim 11, wherein the image processing apparatus further includes
a drawing control circuit configured to perform drawing control for causing a display apparatus to display the picked-up image, a frame rate of which is different, from the image processing circuit, and
a recording apparatus configured to perform recording processing for recording the picked-up image, the frame rate of which is different, from the image processing circuit.

13. The endoscope system according to claim 11, wherein
the control circuit instructs image processing for facilitating identification of the swallow object in the picked-up image in the image processing circuit.

14. The endoscope system according to claim 13, wherein
the control circuit sets an image pickup frame rate at a time of image pickup of the swallowing motion to be higher than a standard frame rate when the swallow object is detected in the picked-up image, and sets the image pickup frame rate at the time of the image pickup of the swallowing motion to the standard frame rate when the swallow object is not detected in the picked-up image.

15. The endoscope system according to claim 13, wherein
the control circuit performs image quality setting to emphasize a complementary color component of the color of the swallow object for a region other than an image region of the swallow object in the picked-up image.

* * * * *